United States Patent
Kronemayer et al.

(10) Patent No.: US 8,436,203 B2
(45) Date of Patent: May 7, 2013

(54) PURIFICATION OF CARBOXYLIC ESTERS BY EXTRACTIVE DISTILLATION

(75) Inventors: Helmut Kronemayer, Heidelberg (DE); Ellen Dahlhoff, Limburgerhof (DE); Andreas Lanver, Mannheim (DE)

(73) Assignee: BASF SE, Ludwigshafen (DE)

( * ) Notice: Subject to any disclaimer, the term of this patent is extended or adjusted under 35 U.S.C. 154(b) by 133 days.

(21) Appl. No.: 13/087,844

(22) Filed: Apr. 15, 2011

(65) Prior Publication Data
US 2011/0257427 A1 Oct. 20, 2011

Related U.S. Application Data

(60) Provisional application No. 61/325,437, filed on Apr. 19, 2010.

(51) Int. Cl.
*C07C 67/54* (2006.01)

(52) U.S. Cl.
USPC ......................................... 560/248

(58) Field of Classification Search ............ None
See application file for complete search history.

(56) References Cited

U.S. PATENT DOCUMENTS

| | | | | |
|---|---|---|---|---|
| 2,455,803 A | * | 12/1948 | Pierotti | 203/51 |
| 2,612,468 A | * | 9/1952 | Morrell et al. | 203/53 |
| 4,569,726 A | * | 2/1986 | Berg et al. | 203/56 |
| 5,302,747 A | | 4/1994 | Nelson et al. | |

FOREIGN PATENT DOCUMENTS

| | | |
|---|---|---|
| JP | 10-175916 | 6/1998 |
| WO | WO 2007/099071 A1 | 9/2007 |

* cited by examiner

*Primary Examiner* — Paul A Zucker
(74) *Attorney, Agent, or Firm* — Oblon, Spivak, McClelland, Maier & Neustadt, L.L.P.

(57) ABSTRACT

In a process for purifying carboxylic esters such as ethyl formate, a carboxylic ester to be purified is distilled in the presence of an extractant, preferably by (a) allowing vapor of the carboxylic ester to be purified to ascend in a distillation column; (b) conveying the extractant in countercurrent to the vapor in an extractive distillation column; (c) taking off pure carboxylic ester above the extractive distillation zone. The extractant is, for example, selected from among diols, polyols, open-chain or cyclic amides.

18 Claims, 1 Drawing Sheet

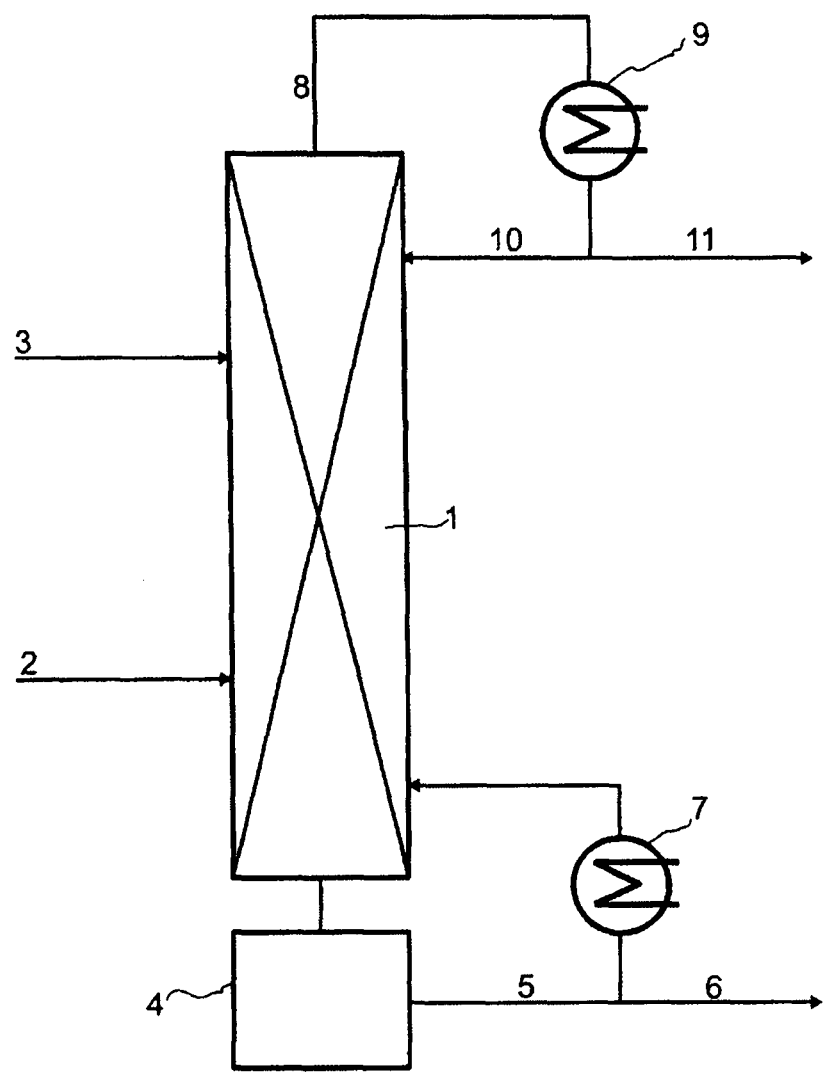

PURIFICATION OF CARBOXYLIC ESTERS BY EXTRACTIVE DISTILLATION

The invention relates to a process for purifying carboxylic esters.

Low molecular weight esters such as formic esters are employed, for example, as fragrances, insecticides, fungicides or in organic synthesis. Processes for preparing low molecular weight esters have been widely described in the literature. An inexpensive preparative method is esterification of carboxylic acid and alcohol with subsequent distillation of the ester. In many cases, this process can be carried out very simply in industry because the product in the form of the ester is the lowest-boiling compound.

U.S. Pat. No. 5,302,747 describes a process in which an inert gas is passed through an esterification mixture which comprises an alcohol and a carboxylic acid and is maintained at least the boiling point of the alcohol in order to drive off the ester.

The preparation of highly pure esters, in particular formic esters, having a purity of greater than 99.5% by weight, in particular greater than 99.8% by weight, is difficult, as will be explained below for the example of the esterification of formic acid with ethanol. The esterification of formic acid with ethanol forms water and ethyl formate. In the distillation of the reaction product, it is possible to separate neither ethanol nor water completely from the ester since both materials form azeotropes with the ester over wide pressure ranges. As a result, highly pure ethyl formate cannot be obtained by this route.

JP 10175916 describes the preparation of highly pure formic esters. The esterification of formic acid and alcohol is carried out by reactive distillation, with the distillate obtained being dewatered by means of acetic anhydride. Although water can be removed by use of desiccants in this process, unreacted alcohol cannot be removed in a comparable way.

WO 2007/099071 describes the preparation of esters by reactive distillation. A carboxylic acid, an alcohol and an entrainer are introduced into a reaction column. The bottom stream comprises the ester formed and unreacted carboxylic acid. The overhead stream comprises unreacted alcohol, water and entrainer.

It is an object of the invention to provide an efficient process for purifying carboxylic esters.

The object is achieved according to the invention by a process for purifying carboxylic esters, wherein a carboxylic ester is distilled in the presence of an extractant.

The process is suitable for purifying low molecular weight carboxylic esters which can be vaporized without decomposition. Possible esters are, in particular, the esters of $C_1$-$C_5$-carboxylic acids with $C_1$-$C_5$-alcohols, e.g. methyl formate, ethyl formate, propyl formate, isopropyl formate, n-butyl formate, sec-butyl formate and n-pentyl formate, methyl acetate, ethyl acetate, propyl acetate, isopropyl acetate, n-butyl acetate, sec-butyl acetate and n-pentyl acetate. The carboxylic ester is preferably a formic ester, in particular ethyl formate.

The impurities comprised in the carboxylic ester to be purified are generally selected from among water, alcohol and free carboxylic acid. The alcohol and the free carboxylic acid generally correspond to the alcohol and carboxylic acid constituents of the carboxylic ester to be purified. However, the alcohol and the free carboxylic acid can also comprise a foreign alcohol and/or a foreign carboxylic acid.

The carboxylic ester to be purified can be, for example, a crude distillate from an esterification reaction or transesterification reaction.

The purity of the carboxylic ester to be purified is generally from 50 to 99.5% by weight, usually from 95 to 99% by weight.

The pure carboxylic ester obtained by the process of the invention generally has a purity of at least 99.5% by weight, preferably at least 99.8% by weight. The purity of the carboxylic ester can be determined, for example, by gas chromatography, ion chromatography, titrimetric methods or pH measurements.

The process of the invention can be carried out in a simple way by heating a mixture of the carboxylic ester to be purified and the extractant to boiling and collecting and condensing the vapor of the pure carboxylic ester.

However, the distillation is preferably carried out as a fractional distillation. Here, all apparatuses customary for distillation, as are described, for example, in Kirk-Othmer, Encyclopedia of Chemical Technology, 3rd Ed., Vol. 7, John Wiley & Sons, New York, 1979, page 870-881, can be used for the distillation.

In a preferred embodiment,
(a) vapor of the carboxylic ester to be purified is allowed to ascend in a distillation column;
(b) the extractant is conveyed in countercurrent to the vapor in an extractive distillation zone;
(c) pure carboxylic ester is taken off above the extractive distillation zone.

For the purposes of the present invention, an "extractive distillation zone" is a section of a column in which the carboxylic ester to be purified and the extractant come into contact with one another under conditions of an extractive distillation. The extractive distillation makes use of the phenomenon that the fugacities of the constituents of the mixture to be separated are altered by addition of the extractant. Extractants used according to the invention selectively increase the relative fugacity of the carboxylic ester. For this reason, the carboxylic ester preferably goes into the low-boiling overhead product in the distillation in the presence of the extractant while the impurities such as carboxylic acid, alcohol and water are found in the extract, i.e. the higher-boiling bottom product from the distillation.

The process can be carried out batchwise, for which purpose the carboxylic ester to be purified is placed in a steel pot. The initially charged carboxylic ester to be purified is heated to boiling and the vapor is passed through the distillation column. The extractant is introduced into the distillation column at the top or preferably at the side and conveyed in countercurrent to the vapor. The extractant collects together with the impurities in the steel pot.

As an alternative, the process can be carried out continuously, for which purpose the carboxylic ester to be purified is introduced into the distillation column below the extractive distillation zone or into the bottom of the distillation column and an extractant-comprising stream is taken off from the bottom.

The pure carboxylic ester is taken off as side offtake fraction above the extractive distillation zone or as overhead fraction, preferably as overhead fraction. For this purpose, the distillation column is provided with facilities for condensing and collecting the overhead product. Part of the overhead condensate can be returned as runback to the column via a condensate divider. The other part of the condensate is taken off as product.

The distillation can be carried out at subatmospheric pressure, atmospheric pressure or superatmospheric pressure. A preferred pressure range is from 15 mbar to 10 bar, particularly preferably from 0.5 to 1.5 bar. The distillation can be carried out in a temperature range (temperature at the bottom) of from 20° to 250° C., preferably at least 50° C.

The distillation column preferably comprises internals which comprise trays, rotating internals, random and/or ordered packings.

In the case of column trays, possibilities are (i) trays having holes or slits in the bottom plate; (ii) trays having necks or chimneys which are covered by bubble caps, caps or hoods; (iii) trays having holes in the bottom plate which are covered by movable valves; (iv) trays having special constructions.

In columns having rotating internals, the runback is either sprayed by rotating funnels or spread as film on a heated tube wall by means of a rotor.

The columns used can have random beds comprising various packing elements. The latter can comprise all suitable materials such as steel, stainless steel, nickel-based alloys such as HC, copper, carbon, stoneware, porcelain, glass, plastics, and be present in various shapes such as spheres, rings having smooth or profiled surfaces, rings having internal webs or passages through the wall, wire mesh rings, saddle bodies and spirals.

Packings having a regular geometry can comprise, for example, metal sheets or woven meshes. Examples of such packings are Sulzer mesh packings BX composed of metal or plastic, Sulzer lamellar packings Mellapack made of metal sheet, structured packings from Sulzer (Optiflow), Montz (BSH) and Kühni (Rombopack).

The distillation column is provided with facilities for bottom heating. Possibilities here are vaporizers which are built into the bottom of the column, for example a Robert vaporizer or a circuit having an external vaporizer, e.g. shell-and-tube or plate heat exchanger. Circulation is then, for example, forced circulation or natural convection.

Classes of substances which are suitable as extractant are preferably diols, polyols, open-chain or cyclic amides and mixtures of the classes of substances mentioned.

As suitable diols and polyols, mentioned may be made by way of example of ethylene glycol, diethylene glycol, triethylene glycol, polyethylene glycol, 1,3-propanediol, 2-methyl-1,3-propanediol, 1,4-butanediol, dipropylene glycol, 1,5-pentanediol, 1,6-hexanediol and glycerol.

As suitable open-chain or cyclic amides, mention may be made by way of example of formamide, N-methylformamide, N,N-dimethylformamide, N-methylpyrrolidone, acetamide and N-methylcaprolactam.

The extractant preferably has a boiling point (at atmospheric pressure) which is at least 30° C. higher, in particular at least 100° C. higher, than the boiling point (at atmospheric pressure) of the carboxylic ester to be purified.

Diols or polyols having from 3 to 5 OH groups are preferably used as polar extractant. Particularly preferred diols and polyols are ethylene glycol, 1,4-butanediol, 2-methyl-1,3-propanediol, among which ethylene glycol is particularly preferred.

Ionic liquids are also suitable as extractants. For the purposes of the present invention, ionic liquids are salts having a melting point below 100° C., preferably below 80° C.

Preference is given to ionic liquids whose cation constituent comprises at least one five- or six-membered heterocycle, in particular a five-membered heterocycle, which has at least one nitrogen atom and optionally an oxygen or sulfur atom; particular preference is given to compounds which comprise at least one five- or six-membered heterocycle comprising one, two or three nitrogen atoms and optionally a sulfur or oxygen atom, very particularly preferably those having two nitrogen atoms. Further preference is given to aromatic heterocycles.

Particularly preferred compounds are compounds which have a molar mass of less than 1000 g/mol, very particularly preferably less than 600 g/mol and in particular less than 400 g/mol.

Preferred cations are selected from among the compounds of the formulae (I.a) to (I.w),

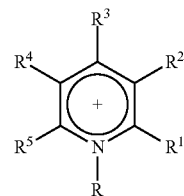

(I.a)

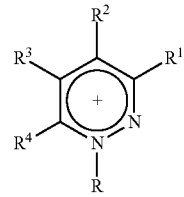

(I.b)

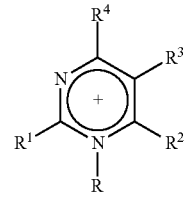

(I.c)

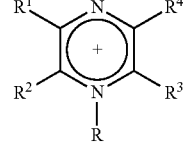

(I.d)

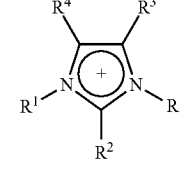

(I.e)

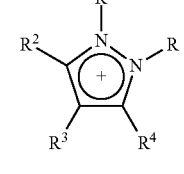

(I.f)

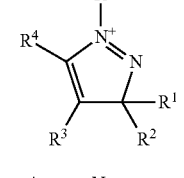

(I.g)

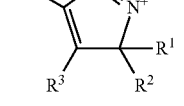

(I.g')

-continued
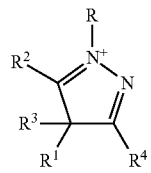 (I.h)
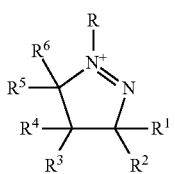 (I.i)
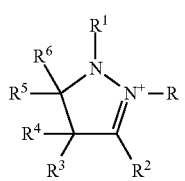 (I.j)
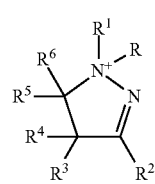 (I.j′)
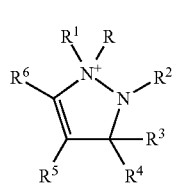 (I.k)
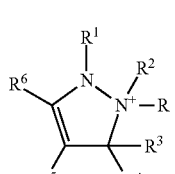 (I.k′)
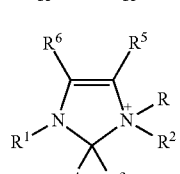 (I.l)
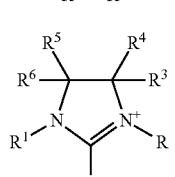 (I.m)
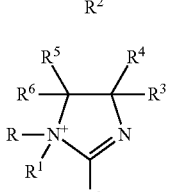 (I.m′)
-continued
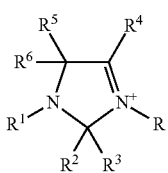 (I.n)
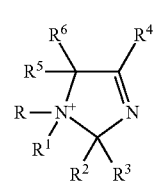 (I.n′)
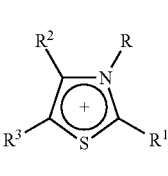 (I.o)
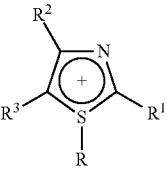 (I.o′)
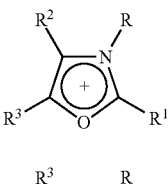 (I.p)
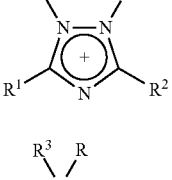 (I.q)
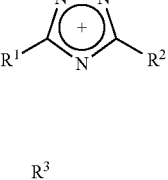 (I.q′)
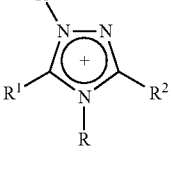 (I.q″)
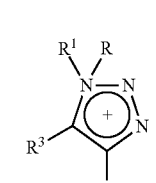 (I.r)

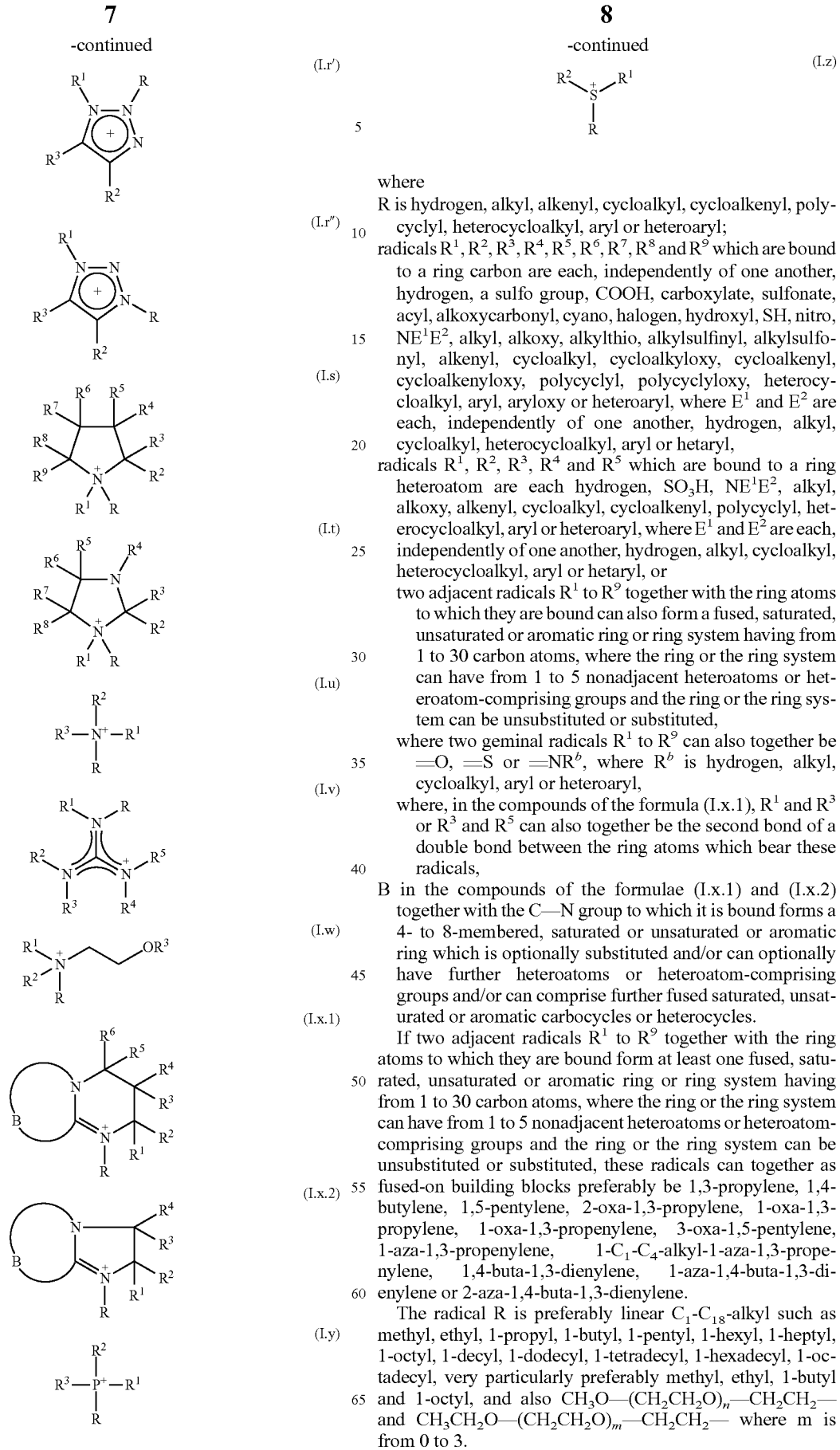

where
R is hydrogen, alkyl, alkenyl, cycloalkyl, cycloalkenyl, polycyclyl, heterocycloalkyl, aryl or heteroaryl;
radicals $R^1$, $R^2$, $R^3$, $R^4$, $R^5$, $R^6$, $R^7$, $R^8$ and $R^9$ which are bound to a ring carbon are each, independently of one another, hydrogen, a sulfo group, COOH, carboxylate, sulfonate, acyl, alkoxycarbonyl, cyano, halogen, hydroxyl, SH, nitro, $NE^1E^2$, alkyl, alkoxy, alkylthio, alkylsulfinyl, alkylsulfonyl, alkenyl, cycloalkyl, cycloalkyloxy, cycloalkenyl, cycloalkenyloxy, polycyclyl, polycyclyloxy, heterocycloalkyl, aryl, aryloxy or heteroaryl, where $E^1$ and $E^2$ are each, independently of one another, hydrogen, alkyl, cycloalkyl, heterocycloalkyl, aryl or hetaryl,
radicals $R^1$, $R^2$, $R^3$, $R^4$ and $R^5$ which are bound to a ring heteroatom are each hydrogen, $SO_3H$, $NE^1E^2$, alkyl, alkoxy, alkenyl, cycloalkyl, cycloalkenyl, polycyclyl, heterocycloalkyl, aryl or heteroaryl, where $E^1$ and $E^2$ are each, independently of one another, hydrogen, alkyl, cycloalkyl, heterocycloalkyl, aryl or hetaryl, or
two adjacent radicals $R^1$ to $R^9$ together with the ring atoms to which they are bound can also form a fused, saturated, unsaturated or aromatic ring or ring system having from 1 to 30 carbon atoms, where the ring or the ring system can have from 1 to 5 nonadjacent heteroatoms or heteroatom-comprising groups and the ring or the ring system can be unsubstituted or substituted,
where two geminal radicals $R^1$ to $R^9$ can also together be =O, =S or =$NR^b$, where $R^b$ is hydrogen, alkyl, cycloalkyl, aryl or heteroaryl,
where, in the compounds of the formula (I.x.1), $R^1$ and $R^3$ or $R^3$ and $R^5$ can also together be the second bond of a double bond between the ring atoms which bear these radicals,
B in the compounds of the formulae (I.x.1) and (I.x.2) together with the C—N group to which it is bound forms a 4- to 8-membered, saturated or unsaturated or aromatic ring which is optionally substituted and/or can optionally have further heteroatoms or heteroatom-comprising groups and/or can comprise further fused saturated, unsaturated or aromatic carbocycles or heterocycles.

If two adjacent radicals $R^1$ to $R^9$ together with the ring atoms to which they are bound form at least one fused, saturated, unsaturated or aromatic ring or ring system having from 1 to 30 carbon atoms, where the ring or the ring system can have from 1 to 5 nonadjacent heteroatoms or heteroatom-comprising groups and the ring or the ring system can be unsubstituted or substituted, these radicals can together as fused-on building blocks preferably be 1,3-propylene, 1,4-butylene, 1,5-pentylene, 2-oxa-1,3-propylene, 1-oxa-1,3-propylene, 1-oxa-1,3-propenylene, 3-oxa-1,5-pentylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The radical R is preferably linear $C_1$-$C_{18}$-alkyl such as methyl, ethyl, 1-propyl, 1-butyl, 1-pentyl, 1-hexyl, 1-heptyl, 1-octyl, 1-decyl, 1-dodecyl, 1-tetradecyl, 1-hexadecyl, 1-octadecyl, very particularly preferably methyl, ethyl, 1-butyl and 1-octyl, and also $CH_3O$—$(CH_2CH_2O)_n$—$CH_2CH_2$— and $CH_3CH_2O$—$(CH_2CH_2O)_m$—$CH_2CH_2$— where m is from 0 to 3.

Preference is given to the radicals $R^1$ to $R^9$ each being, independently of one another, hydrogen; $C_1$-$C_{18}$-alkyl such as methyl, ethyl, 1-butyl, 1-pentyl, 1-hexyl, 1-heptyl, 1-octyl; phenyl; 2-hydroxyethyl; 2-cyanoethyl; 2-(alkoxycarbonyl) ethyl such as 2-(methoxycarbonyl)ethyl, 2-(ethoxycarbonyl) ethyl or 2-(n-butoxycarbonyl)ethyl; N,N—($C_1$-$C_4$-dialkyl) amino such as N,N-dimethylamino or N,N-diethylamino; chlorine and also radicals of oligoalkylene glycol, e.g. $CH_3O$—$(CH_2CH_2O)_n$—$CH_2CH_2$— or $CH_3CH_2O$—$(CH_2CH_2O)_n$—$CH_2CH_2$— where n is from 0 to 3.

Among the abovementioned heterocyclic cations, preference is given to the imidazolium ions, imidazolinium ions, pyridinium ions, pyrazolinium ions and pyrazolium ions. Particular preference is given to the imidazolium ions and cations of 1,5-diazabicyclo[4.3.0]non-5-ene (DBN) and 1,8-diazabicyclo[5.4.0]undec-7-ene (DBU).

The anion of the ionic liquid is, for example, selected from the group of pseudohalides and halogen-comprising compounds of the formulae:
$BF_4^-$, $PF_6^-$, $CF_3SO_3^-$, $(CF_3SO_3)_2N^-$, $CF_3CO_2^-$, $CCl_3CO_2^-$, $CN^-$, $SCN^-$, $OCN^-$;

the group of sulfates, sulfites and sulfonates of the general formulae:
$SO_4^{2-}$, $HSO_4^-$, $SO_3^{2-}$, $HSO_3^-$, $R^cSO_3^-$, $R^cSO_3^-$;

the group of phosphates of the general formulae:
$PO_4^{3-}$, $HPO_4^{2-}$, $H_2PO_4^-$, $R^cPO_4^{2-}$, $HR^cPO_4^-$, $R^cR^dPO_4^-$;

the group of phosphonates and phosphinates of the general formulae:
$R^cHPO_3^-$, $R^cR^dPO_2^-$, $R^cR^dPO_3^-$;

the group of phosphites of the general formulae:
$PO_3^{3-}$, $HPO_3^{2-}$, $H_2PO_3^-$, $R^cPO_3^{2-}$, $R^cHPO_3^-$, $R^cR^dPO_3^-$;

the group of phosphonites and phosphinites of the general formulae:
$R^cR^dPO_2^-$, $R^cHPO_2^-$, $R^cR^dPO^-$, $R^cHPO^-$;

the group of carboxylic acids of the general formula:
$R^cCOO^-$.

Preference is given to the radicals $R^c$, $R^d$ each being, independently of one another, hydrogen; $C_1$-$C_{30}$-alkyl, alkyl persubstituted or partially substituted by halogen, or $C_6$-$C_{14}$-aryl.

Preferred anions are formate, acetate, propionate, butyrate, lactate, saccharinate, carbonate, hydrogencarbonate, sulfate, sulfite, $C_1$-$C_4$-alkylsulfates, methanesulfonate, tosylate, trifluoroacetate, $C_1$-$C_4$-dialkylphosphates and hydrogensulfate.

Particularly suitable ionic liquids are 1-ethyl-3-methylimidazolium acetate and 1-n-butyl-3-methylimidazolium acetate.

The invention is illustrated by the accompanying drawings and the following examples.

FIG. 1 schematically shows a plant suitable for carrying out the process of the invention.

The carboxylic ester to be purified is introduced via the feed line 2 into a distillation column 1 in the lower region of the distillation column 1 and the extractant is introduced via the feed line 3 into the upper region of the distillation column 1. A bottom product consisting essentially of extractant and impurities is taken off from the bottom 4 via the line 5 and partly recirculated via the heater 7 to the distillation column 1 and partly discharged via line 6. Overhead product, which consists essentially of the pure carboxylic ester, is taken off via line 8 and condensed in the condenser 9. Part of the condensate is recirculated via line 10 to the distillation column 1. Pure carboxylic ester is taken off via line 11.

EXAMPLE 1 (REFERENCE EXAMPLE)

About 558 g of formic acid (98-100% strength by weight) were reacted with about 276 g of ethanol (technical grade) in a stirred vessel. About 5.8 g of methanesulfonic acid served as catalyst. After stirring for 3 hours, the reaction mixture was distilled off via a column (30 cm high, packed with glass rings). This gave about 348 g of distillate having the following composition:
about 96.5% by weight of ethyl formate,
about 2.5% by weight of water,
about 0.5% by weight of ethanol and
about 0.5% by weight of other compounds (including formic acid).

EXAMPLE 2

About 664 g of a mixture of about 99.2% by weight of ethyl formate, 0.02% by weight of water, 0.8% by weight of ethanol and 0.4% by weight of formic acid was fed together with about 104 g of 1-ethyl-3-methylimidazolium acetate into a thin film evaporator. This gave about 232 g of distillate having the composition:
about 99.7% by weight of ethyl formate,
about 0.01% by weight of water,
about 0.23% by weight of ethanol,
about 0.05% by weight of formic acid and
about 0.01% by weight of other compounds.

EXAMPLE 3

In a process simulation calculation, a mixture having the composition about 98.0% by weight of ethyl formate, 0.5% by weight of water, 1.0% by weight of ethanol, 0.5% by weight of formic acid was fed to a column having 20 theoretical plates. About 100 g/h of the mixture were introduced into the middle of the lower half of the column and about 56 g/h of ethylene glycol into the middle of the upper part column. The distillation was carried out at atmospheric pressure. A temperature at the bottom of about 68° C. was set. At the bottom of the column, the ethylene glycol fed in together with the major part of the impurities in the feed mixture was discharged. At the top of the column, the overhead stream was condensed at 10° C. and, with the aid of a runback divider, about half of the condensate was returned as runback to the column and the other half was taken off. This gave about 95 g/h of distillate having the composition:
about 99.9% by weight of ethyl formate,
<0.01% by weight of water,
about 0.1% by weight of ethanol,
<0.01% by weight of formic acid and
<0.01% by weight of other compounds.

EXAMPLE 4

About 860 g of a mixture having the composition about 98.2% by weight of ethyl formate, 0.6% by weight of water, 1.2% by weight of ethanol were placed in the bottom of a 60 cm long column filled with packing elements to increase the separation performance. The bottom was heated to boiling by means of a heated jacket. Finally, about 300 g/h of ethylene glycol were introduced into the middle of the upper part of the column. The distillation was carried out at atmospheric pressure. At the top of the column, the overhead stream was condensed by means of a water-cooled condenser (about 10° C.) and, with the aid of a runback divider, about one fifth of the condensate was returned as runback to the column and the remaining part of the condensate was taken off. Over a period of 2 hours, this gave about 312 g/h of distillate having the composition:
about 99.9% by weight of ethyl formate,
about 0.01% by weight of water,
about 0.08% by weight of ethanol and
<0.01% by weight of other compounds.

COMPARATIVE EXAMPLE 1

About 414 g of a mixture having the composition about 96.2% by weight of ethyl formate, 0.8% by weight of ethanol, 3.5% by weight of formic acid were placed in the bottom of a 60 cm long column filled with packing elements to increase the separation performance. The bottom was heated to boiling by means of a heated jacket. The distillation was carried out at atmospheric pressure. At the top of the column, the overhead stream was condensed by means of a water-cooled condenser (about 10° C.) and, with the aid of a runback divider, about two thirds of the condensate was returned as runback to the column and the remaining part of the condensate was taken off. Over a period of 3 hours, this gave about 341 g/h of distillate having the composition:
about 99.0% by weight of ethyl formate,
about 0.9% by weight of ethanol and
about 0.1% by weight of formic acid.

COMPARATIVE EXAMPLE 2

About 860 g of a mixture having the composition about 98.2% by weight of ethyl formate, 0.6% by weight of water, 1.2% by weight of ethanol were placed in the bottom of a 60 cm long column filled with packing elements to increase the separation performance. The bottom was heated to boiling by means of a heated jacket. The distillation was carried out at atmospheric pressure. At the top of the column, the overhead stream was condensed by means of a water-cooled condenser (about 10° C.) and, with the aid of a runback divider, about one fifth of the condensate was returned as runback to the column and the remaining part of the condensate was taken off. This gave distillate having the composition:
about 98% by weight of ethyl formate,
about 0.9% by weight of water,
about 1.0% by weight of ethanol and
<0.1% by weight of other compounds.

The invention claimed is:

1. A process for purifying a carboxylic ester, comprising distilling a composition comprising the carboxylic ester in the presence of an extractant, and recovering the purified carboxylic ester, wherein the extractant is an ionic liquid.

2. The process according to claim 1, wherein
  (a) vapor of the carboxylic ester to be purified is allowed to ascend in a distillation column;
  (b) the extractant is conveyed in countercurrent to the vapor in an extractive distillation zone;
  (c) pure carboxylic ester is taken off above the extractive distillation zone.

3. The process according to claim 2, wherein the carboxylic ester to be purified is placed in a steel pot and then heated to boiling, prior to step (a).

4. The process according to claim 2, wherein the carboxylic ester to be purified is introduced into the distillation column below the extractive distillation zone or into the bottom of the distillation column and an extractant-comprising stream is taken off from the bottom.

5. The process according to claim 2, wherein the pure carboxylic ester is taken off as overhead fraction.

6. The process according to claim 1, wherein the boiling point of the extractant is at least 30° C. higher than the boiling point of the carboxylic ester to be purified.

7. The process according to claim 1, wherein the impurities comprised in the carboxylic ester to be purified comprises at least one of water, alcohol and free carboxylic acid.

8. The process according to claim 1, wherein the carboxylic ester to be purified is ethyl formate.

9. The process according to claim 1, wherein the pure carboxylic ester has a purity of at least 99.5% by weight.

10. A process for purifying a carboxylic acid ester, comprising distilling a composition comprising the carboxylic ester, water, an alcohol, and a free carboxylic acid in the presence of an extractant selected from the group consisting of diols, polyols, open-chain or cyclic amides, and ionic liquids, and recovering the purified carboxylic ester.

11. The process according to claim 10, wherein the carboxylic ester is an ester of a $C_1$-$C_5$ carboxylic acid with a $C_1$-$C_5$ alcohol.

12. The process according to claim 10 wherein
  (a) vapor of the carboxylic ester to be purified is allowed to ascend in a distillation column;
  (b) the extractant is conveyed in countercurrent to the vapor in an extractive distillation zone;
  (c) pure carboxylic ester is taken off above the extractive distillation zone.

13. The process according to claim 12, wherein the carboxylic ester to be purified is placed in a steel pot and then heated to boiling, prior to step (a).

14. The process according to claim 12, wherein the carboxylic ester to be purified is introduced into the distillation column below the extractive distillation zone or into the bottom of the distillation column and an extractant-comprising stream is taken off from the bottom.

15. The process according to claim 12, wherein the pure carboxylic ester is taken off as overhead fraction.

16. The process according to claim 10, wherein the boiling point of the extractant is at least 30° C. higher than the boiling point of the carboxylic ester to be purified.

17. The process according to claim 10, wherein the carboxylic ester to be purified is ethyl formate.

18. The process according to claim 10, wherein the pure carboxylic ester has a purity of at least 99.5% by weight.

* * * * *